(12) United States Patent
Robar et al.

(10) Patent No.: US 11,426,602 B2
(45) Date of Patent: Aug. 30, 2022

(54) SYSTEM AND METHOD FOR MANUFACTURING BOLUS FOR RADIOTHERAPY USING A THREE-DIMENSIONAL PRINTER

(71) Applicant: Dalhousie University, Halifax (CA)

(72) Inventors: James Robar, Halifax (CA); Shiqin Su, Halifax (CA)

(73) Assignee: ADAPTIIV MEDICAL TECHNOLOGIES INC., Halifax (CA)

( * ) Notice: Subject to any disclaimer, the term of this patent is extended or adjusted under 35 U.S.C. 154(b) by 598 days.

(21) Appl. No.: 16/427,444

(22) Filed: May 31, 2019

(65) Prior Publication Data

US 2019/0282832 A1   Sep. 19, 2019

Related U.S. Application Data

(63) Continuation of application No. 15/157,029, filed on May 17, 2016, now Pat. No. 10,350,435, which is a (Continued)

(51) Int. Cl.
*A61N 5/10* (2006.01)
*A61B 6/03* (2006.01)
(Continued)

(52) U.S. Cl.
CPC ............ *A61N 5/1031* (2013.01); *A61B 6/032* (2013.01); *A61B 6/5217* (2013.01); (Continued)

(58) Field of Classification Search
CPC .. A61N 5/1031; A61N 5/1048; A61N 5/1049; A61N 5/1071; A61N 5/1075;
(Continued)

(56) References Cited

U.S. PATENT DOCUMENTS

| | | | |
|---|---|---|---|
| 6,703,632 B1 * | 3/2004 | Macklis | A61N 5/10 |
| | | | 250/515.1 |
| 2004/0122308 A1 * | 6/2004 | Ding | A61N 5/1048 |
| | | | 600/407 |

(Continued)

OTHER PUBLICATIONS

Perkins et al. "A Custom Three-dimensional Electron Bolus Technique for Optimization of Postmastectomy Irradiation". Int. J. Radiation Oncology Biol. Phys. 51.4 (2001): 1142-1151. (Year: 2001).*

*Primary Examiner* — Carrie R Dorna
(74) *Attorney, Agent, or Firm* — Hill & Schumacher

(57) ABSTRACT

Disclosed herein are systems, methods, and computer-readable storage devices for manufacturing patient-specific bolus for use in targeted radiotherapy treatment. Based on dose calculations without a bolus and based on three-dimensional scan data of a patient, the example system generates a model of a bolus for targeting radiotherapy treatment to a planning target volume or target region within the patient. The system can perform several iterations to generate a resulting model for the bolus. Then, the system can generate instructions for controlling a three-dimensional printer to generate the bolus that conforms to the patient's skin surface while also specifically targeting the planning target volume for the radiotherapy treatment. In this way, the amount of radiotherapy treatment administered to other tissue is reduced, while the costs, time, and human involvement in creating the bolus are significantly reduced.

20 Claims, 12 Drawing Sheets

Related U.S. Application Data continuation-in-part of application No. PCT/CA2014/051128, filed on Nov. 26, 2014.

(60) Provisional application No. 61/909,789, filed on Nov. 27, 2013.

(51) Int. Cl.
*A61B 6/00* (2006.01)
*B29L 31/00* (2006.01)
*B33Y 50/02* (2015.01)
*B33Y 80/00* (2015.01)
*B29K 67/00* (2006.01)

(52) U.S. Cl.
CPC ......... *A61N 5/1048* (2013.01); *A61N 5/1075* (2013.01); *A61N 2005/1034* (2013.01); *A61N 2005/1076* (2013.01); *A61N 2005/1087* (2013.01); *A61N 2005/1089* (2013.01); *A61N 2005/1096* (2013.01); *A61N 2005/1097* (2013.01); *B29K 2067/046* (2013.01); *B29K 2995/0056* (2013.01); *B29L 2031/753* (2013.01); *B33Y 50/02* (2014.12); *B33Y 80/00* (2014.12)

(58) Field of Classification Search
CPC .... A61N 2005/1034; A61N 2005/1095; A61N 2005/1096; A61N 2005/1097; A61N 2005/1076
See application file for complete search history.

(56) References Cited

U.S. PATENT DOCUMENTS

| | | | |
|---|---|---|---|
| 2007/0276229 A1* | 11/2007 | Adler | A61B 90/17 600/426 |
| 2010/0070236 A1* | 3/2010 | Campana | A61N 5/10 702/167 |
| 2010/0195793 A1* | 8/2010 | Nelms | A61N 5/103 378/65 |
| 2014/0193058 A1* | 7/2014 | Bharat | A61N 5/1037 382/131 |
| 2014/0330417 A1* | 11/2014 | Keane | A61B 90/18 700/98 |

* cited by examiner

SYSTEM AND METHOD FOR MANUFACTURING BOLUS FOR RADIOTHERAPY USING A THREE-DIMENSIONAL PRINTER

CROSS-REFERENCE TO RELATED APPLICATIONS

This application is a continuation of International Application No. PCT/CA2014/051128 (published as WO 2015/077881), filed on Nov. 26, 2014, which claims priority to U.S. Provisional Patent Application No. 61/909,789, filed on Nov. 27, 2013; the contents of both applications are herein incorporated by reference in their entirety.

BACKGROUND

1. Technical Field

The present disclosure relates to manufacturing bolus for use in radiotherapy and more specifically to customized, user-specific bolus for accurately targeting a specific treatment area. The disclosure also addresses creating bolus for different types of therapy, including photon therapy, electron therapy, and proton therapy. The disclosure also describes how a bolus can be incorporated into an immobilization device, and how a custom, 3D-printed bolus can incorporate dosimeter functionality.

2. Introduction

Radiotherapy is a treatment for disease in which an affected part of the body of a patient is exposed to ionizing radiation. For a range of treatment applications, an adequate surface dose is required, particularly in the presence of superficial target volumes. Since megavoltage radiation beams do not deposit maximal dose at the skin surface, in these cases surface dose can be increased by overlaying a tissue equivalent material, called bolus. Bolus is most commonly used in conjunction with electron therapy which is well suited to treatment of superficial lesions with a single beam. A second purpose of bolus is controlling the depth in tissue at which a therapeutic dose of radiation is deposited, and modulating this depth as a function of position across the beam.

Currently, radiation therapists manually create bolus. For example, a radiation therapist can apply wax or thermoplastic sheets to the patient surface. Often, a radiation therapist heats the wax or other material to make it more pliable or malleable. The radiation therapist can apply the bolus material in one or more layers to conform to the patient surface. Often the radiation therapist attempt to manually create a regular geometry or a flat surface at the location of beam incidence. The patient and radiation therapist must then wait while the bolus material cools.

This manual approach is limited in regard to accuracy, practicality and quality of the delivered treatment. First, this process is labor intensive because it involves manual application of bolus material. This occupies the patient, potentially multiple staff members, as well as clinic space, often in an expensive or valuable computed tomography (CT) suite. Second, the bolus should conform well to the patient skin, even in situations where the geometry is complex, such as an outer ear, canthus, lip, or other extremities. The capacity of manually produced bolus to conform to irregular surfaces is limited. Inaccuracy of bolus fabrication can result in air gaps between the bolus and patient surface. Air gaps, in turn, can result in substantial inaccuracies in delivered surface dose, for example, exceeding 10%. In practice, this sometimes prompts filling of air gaps with wet gauze, however the variability in the wetness of the gauze causes inconsistency in delivered dose. Third, bolus is commonly pre-defined in the planning system as a water equivalent, uniform layer on the patient surface. The similarity of the planned and fabricated bolus is limited with regard to both thickness and curvature, particularly in the presence of steep, complex or curved surfaces. This compromises the accuracy of the delivered dose distribution relative to the plan. Fourth, other than controlling the depth of penetration of an electron beam into tissue, manually manufactured bolus does not achieve conformity between the radiation dose and the target volume. Most commonly, the high dose region will encompass the deepest aspect of an irregularly shaped tumor but also a volume of surrounding healthy tissue which would be preferable to avoid exposing to excess radiation.

DETAILED DESCRIPTION

Figure 1:
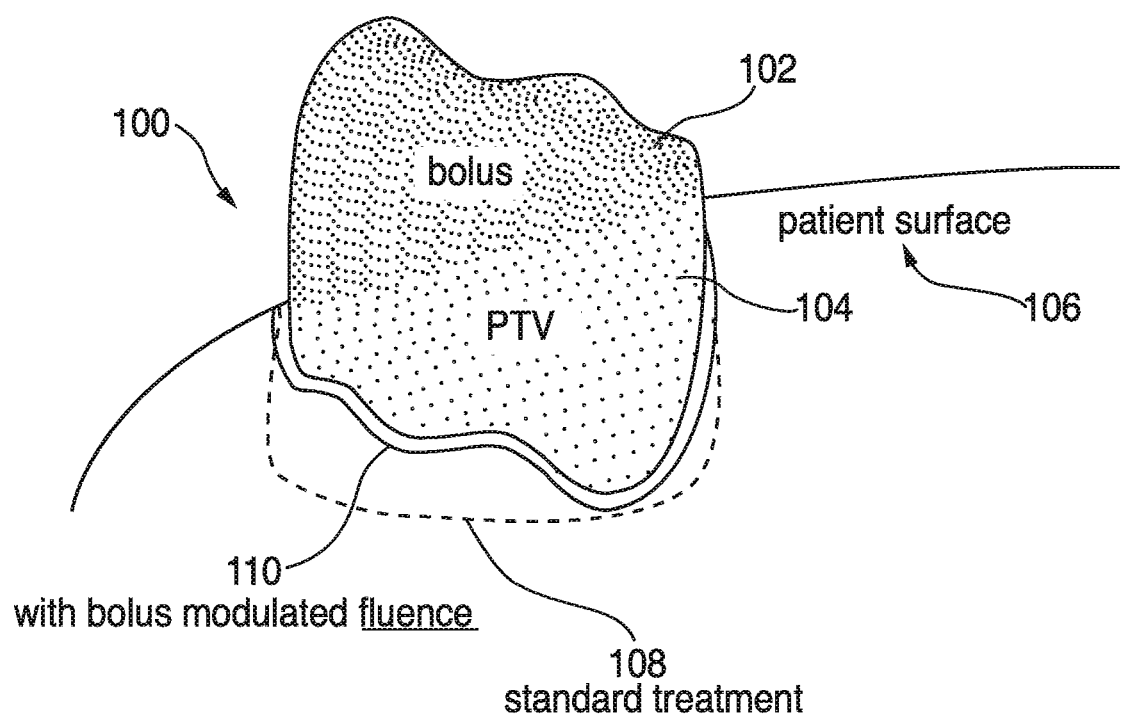
FIG. 1 illustrates an example bolus on an example patient surface.

A system, method and computer-readable storage devices are disclosed which provide a way to plan radiotherapy treatment, such as with a single electron beam or one or more photon beams, using computer models of the patient derived from three-dimensional imaging data, while delivering an adequate dose to the planning target volume (PTV) of the patient while minimizing the dose to surrounding healthy tissues and normal structures of the patient. Bolus can be custom manufactured for patients to achieve this goal, such as with a three-dimensional printer.

The approach described herein can provide several advantages. For example, patients already undergo CT imaging for treatment planning. The example system can design bolus digitally with high accuracy and precision based on this three dimensional data set without the patient's presence. The system can design the bolus so that the upper (proximal) surface of the bolus enhances the dose conformity, dose homogeneity, dose uniformity, quality, or effective area of the radiation delivered plan. Further, the system can manufacture the bolus using additive manufacturing, such as three dimensional printing technology. The printed bolus may be manufactured using polylactic acid (PLA), which is biocompatible. PLA is derived from starches (e.g. corn) and is already used for medical implants in the form of screws, pins, rods, and mesh.

3D printing is a specific form of additive manufacturing. One of the most common methods of 3D printing, and the one explored in this work is Fused Deposition Modeling (FDM). This process has recently has become widely accessible at low cost, such as MakerBot devices. 3D printing involves a fabrication process that uses a CAD model as input to create a 3D physical model by applying many successive layers of the chosen material at a high resolution, such as a resolution of 100 micrometers, although the system can use other resolutions and capabilities.

3D printing provides several advantages over the manual approach to bolus fabrication. Bolus fabrication can be largely automated, and the precision can be substantially improved. Because the fabrication is automated, human error is reduced. Thus, 3D printed bolus can provide improved conformity between bolus and patient surface, reducing the possibility of air cavities which would degrade accuracy of treatment or would provide a dosage above or below what is desired. PLA bolus is durable, unlike traditional wax bolus materials. Increased durability can be particularly important for treatment regimes with the bolus over an extended period of time, such as a regime of 30 daily treatments. A precisely generated bolus can provide a customized, highly conformal dose distribution for each individual patient based on his or her specific needs and situation. 3D printing allows for a clinic or doctor to fabricate optimized bolus designs in-house rather than placing an order to an off-site service which may be expensive or require a lengthy wait. 3D printing can provide a cost reduction, time savings, improved treatment flexibility, and ability to respond to changing clinical demands by modifying the bolus design during the course of the treatment.

Aside from these practical advantages, digital design and 3D printing of bolus can also improve the delivered treatment. Currently, the electron therapy planning process involves the selection of beam energy and electron aperture dimensions to achieve adequate coverage of the Planning Target Volume (PTV). 3D printing allows for customizing the patient surface to optimize the shape of the dose distributions produced at a particular depth and region within the PTV. This concept is illustrated in FIG. 1. FIG. 1 illustrates an example configuration 100 of a bolus 102 on an example patient surface 106 to treat a specific PTV region 104. This example illustrates how the unique shape of the bolus 102 can be tailored to provide treatment to a region 110 tightly surrounding the PTV 104 rather than a larger region 108 associated with standard treatment. The specific shape of the bolus 102 is tailored to match the PTV 104 very closely to avoid treating body tissues which are outside of the PTV 104. When 3D printing bolus, the system can generate a patient-specific bolus without introducing any new steps for the patient since the CT data is typically acquired as part of the treatment planning process.

A bolus 102 can be constructed for multiple different types of radiation therapy. For example, a bolus 102 can be constructed for use in photon therapy, electron therapy, or proton therapy. The propagation and other characteristics of photons, electrons, and protons are different. Thus, different bolus shapes, sizes, thicknesses, and/or constructions can be used to target a treatment dose of radiation to a same body region using different radiation therapies.

Radiation therapy professionals can use a bolus for megavoltage photon therapy, particularly when a maximal dose is required at the patient's skin. A 3D-printed bolus can be produced, based on measurements of the patient's skin contours and the target treatment region within the body. With accurate measurements of the patient's skin and body contours, the 3D-printed bolus can be shaped to mate accurately to the patient surface, even in the presence of very complex geometries, such as the regions around the face, ears, or surgical cavities. As set forth above, while the patient-facing surface of the bolus is shaped based on the body geometry, the non-patient facing surface of the bolus is shaped so that radiation treatments, when applied from one or more points external to the body through the bolus, are directed to affect only a specific desired treatment target region within the body and/or at the surface of the skin.

However, due to differences in the way photons interact and/or propagate compared to electrons and protons, it is difficult to control high-dose conformity (agreement between shapes of the high dose volume and the target) through the use of bolus. Therefore, the system can produce an accurately fitting bolus of a thickness (or variable thickness, if desired) specified by a doctor or other radiation treatment professional, to achieve the required dose of radiation treatment at the surface. Any accurate photon dose calculation can be used in conjunction with this design process. In one example implementation, the system uses the Anisotropic Analytic Algorithm (AAA, from Varian Medical), but many other suitable algorithms exist and can be used interchangeably. Advantages of the approach include but are not limited to (i) bolus design from CT data, resulting in less human involvement in the bolus creation process, (ii) bolus conformity to complex surfaces (e.g., surgical site post-mastectomy), and (iii) specification of thickness or density of bolus (which in turn controls the surface dose).

Since some of the most challenging and common scenarios for use of bolus involve electron beam therapy, many of the examples provided herein focus primarily on that application. While the design of the distal surface (the surface mating to the skin) is based on CT data indicating the surface and contours of the patient, design of the bolus to target the PTV via the proximal surface is non-trivial. Electrons scatter within any medium in a complex way, and thus simple approaches such as ray-tracing are not adequate. An algorithm for bolus design can achieve specific dosimetric goals. The system can incorporate this algorithm in to a common treatment planning approach. The system can provide an interface allowing production of the optimized bolus using 3D printing. The algorithm can operate in conjunction with an external beam planning system, obviating the need to re-implement a system accurate dose calculation. The system can incorporate the electron Monte Carlo (eMC) algorithm. A block diagram 200 of an iterative approach of the algorithm is outlined in FIG. 2.

After calculating an initial dose distribution in absence of bolus 202, the treatment plan, CT set, structures and dose distribution are provided to a system 204 implementing the algorithm. The system 204 calculates an initial approximation of bolus design to achieve conformal coverage of the target volume. The system can provide the bolus design back to the planning system for dose calculation with the bolus design 206. The system can iterate this process in an automated fashion with subsequent cycles also addressing more subtle aspects of improvement of the dose distribution, such as hot-spots, cool spots and optimization of conformity at the edges of the target volume. For example, if the dose calculation with bolus 206 is not acceptable 208, then the system 204 can iterate on the bolus design again. Empirical evidence shows that 2-3 iterations are usually sufficient to achieve high plan quality. If, however, the bolus design is acceptable 208, then the bolus can be exported, such as via an STL file format, to a bolus fabrication device 210, such as a 3D printer. The bolus fabrication device 210 can manufacture the bolus with minimal user intervention. Following manufacture, a doctor or radiation therapist can place the bolus on the patient to confirm that the positioning and fit are proper. If desired, the doctor or radiation therapist can perform an additional CT scan with the bolus in place to collect a final dose calculation with the actual manufactured bolus. The example dose calculation 214 can operate according to the electron Monte Carlo (eMC) algorithm, but can be replaced with any suitably accurate electron dose calculation algorithm. Similarly, for different types of radiation therapy, different algorithms can be applied, such as an algorithm for proton or photon therapy.

Figure 2:
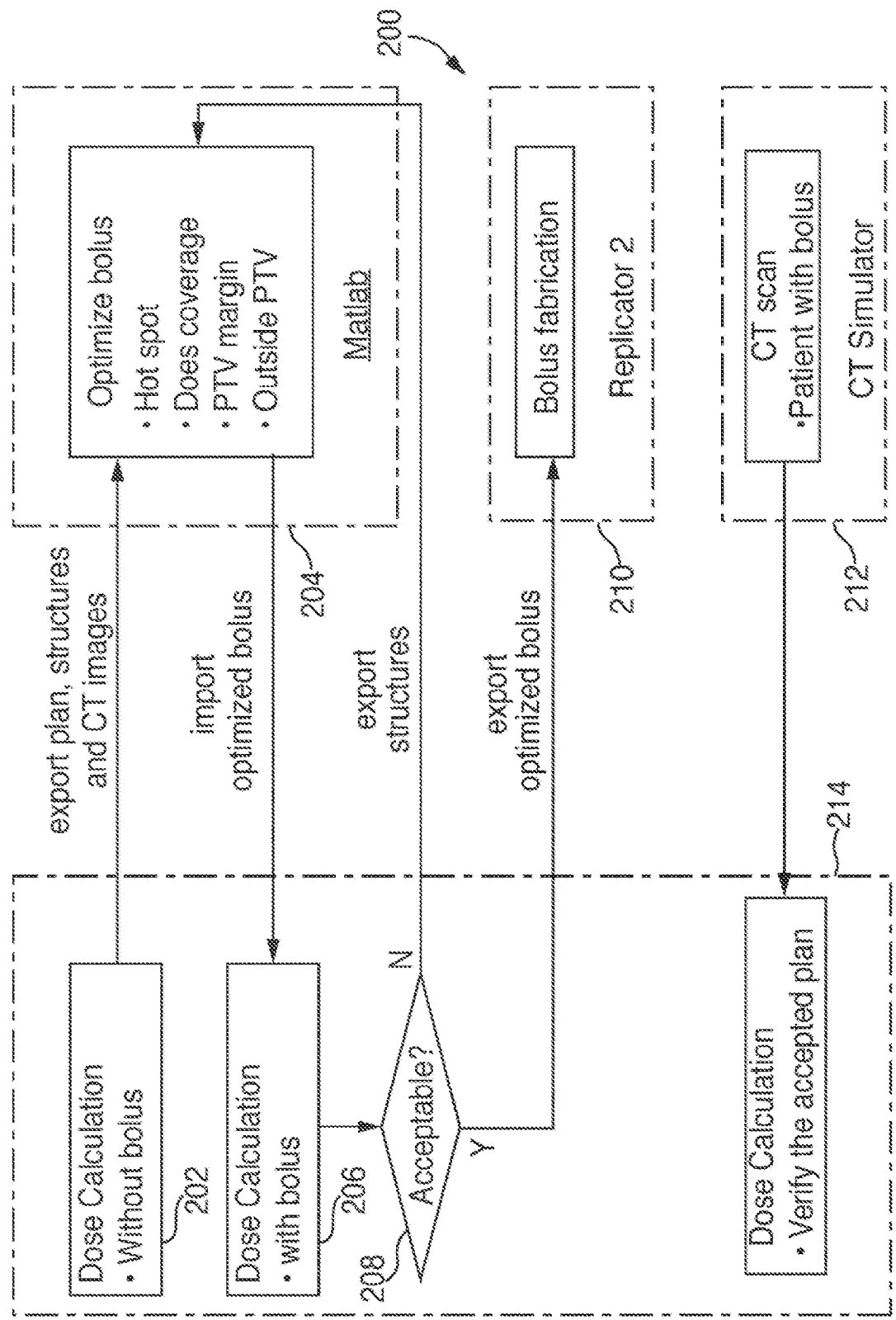
FIG. 2 illustrates an example block diagram of an iterative approach to manufacturing a bolus.

The bolus optimization and design system of FIG. 2 is modular, i.e. the bolus design portion 204 is isolated from the dose calculation portion 202, 206. For proton therapy, the eMC electron calculation algorithm in the treatment planning system could be replaced by a proton dose calculation algorithm. Example algorithms for proton dose calculation may be analytic or Monte Carlo. Some tuning of the bolus optimization algorithm would be required for use in proton therapy applications, notably the parameters of regional modulation and adjustment at Planning Target Volume margin. Some tuning of the bolus optimization algorithm may be required for proton therapy applications, such as the regional smoothing operators to adjust for dose coverage at the distal surface of the PTV, hot- and cold-spots within the PTV, and coverage at the PTV margins.

Figure 9:
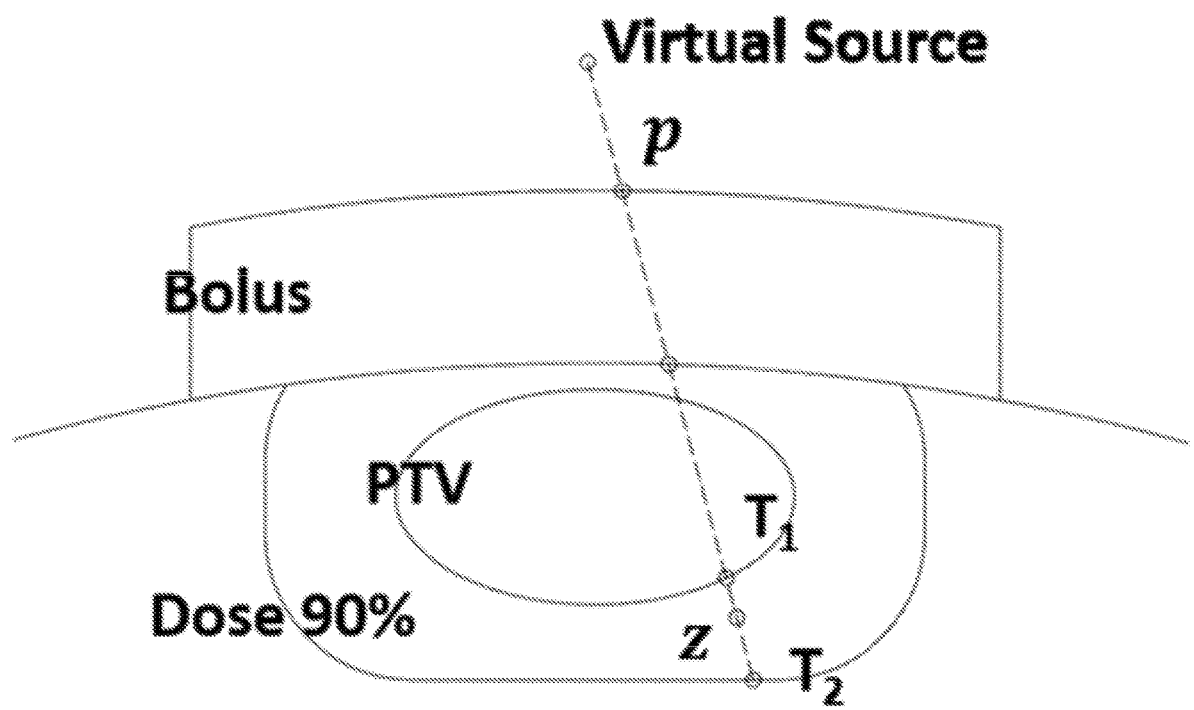
FIG. 9 illustrates an example bolus design calculation.

FIG. 9 illustrates a bolus design calculation. Bolus design is calculated on a grid containing the isocenter and perpendicular to central axis. Bolus thickness is calculated using a grid size of 2.5 mm as default; however a finer grid can be used for improved precision. Structures exported from Eclipse (i.e., 'bolus', 'PTV', 'Dose 90%' and 'Hot Spot' (if required)), are segmented into distal (i.e., deeper) and proximal (i.e., shallower) surfaces according to the maximum and minimum lateral coordinates. Ray lines are traced from the virtual source to each point on the grid, and extended to the distal side of PTV and 90% isodose surfaces. For ray lines intersecting the PTV, the distance $z_{real} = T_1 T_2$ is calculated.

Since patients typically contain tissue inhomogeneities, $z_{real}$ is converted to an effective distance $z_{eff}$ using the coefficient of equivalent thickness (CET) method. The effective shift of bolus thickness (SBT) of a certain point p on the grid is given by:

$$SBT_p = \frac{1}{CET(\text{Bolus})} \int_{T2}^{T1} CET(z) dz$$

where CET(z) is the density at point z relative to that of water. Note that because the initial plan is calculated with no bolus and the requirement is complete coverage of the PTV by the 90% dose surface, all $SBT_p$ values will be positive in the first iteration. In subsequent iterations, $SBT_p$ values are used to adjust the design of the bolus resulting from the previous iteration (FIG. 10(a)). The density is obtained from the HU to density lookup table in the planning system which, in turn, was obtained during eMC commissioning from a HU calibration phantom (Catphan, the Phantom Laboratory, Salem, N.Y.). Each iteration of the algorithm includes calculation by the eMC algorithm such that subsequent modifications are based on an accurate dose distribution.

Figure 10:
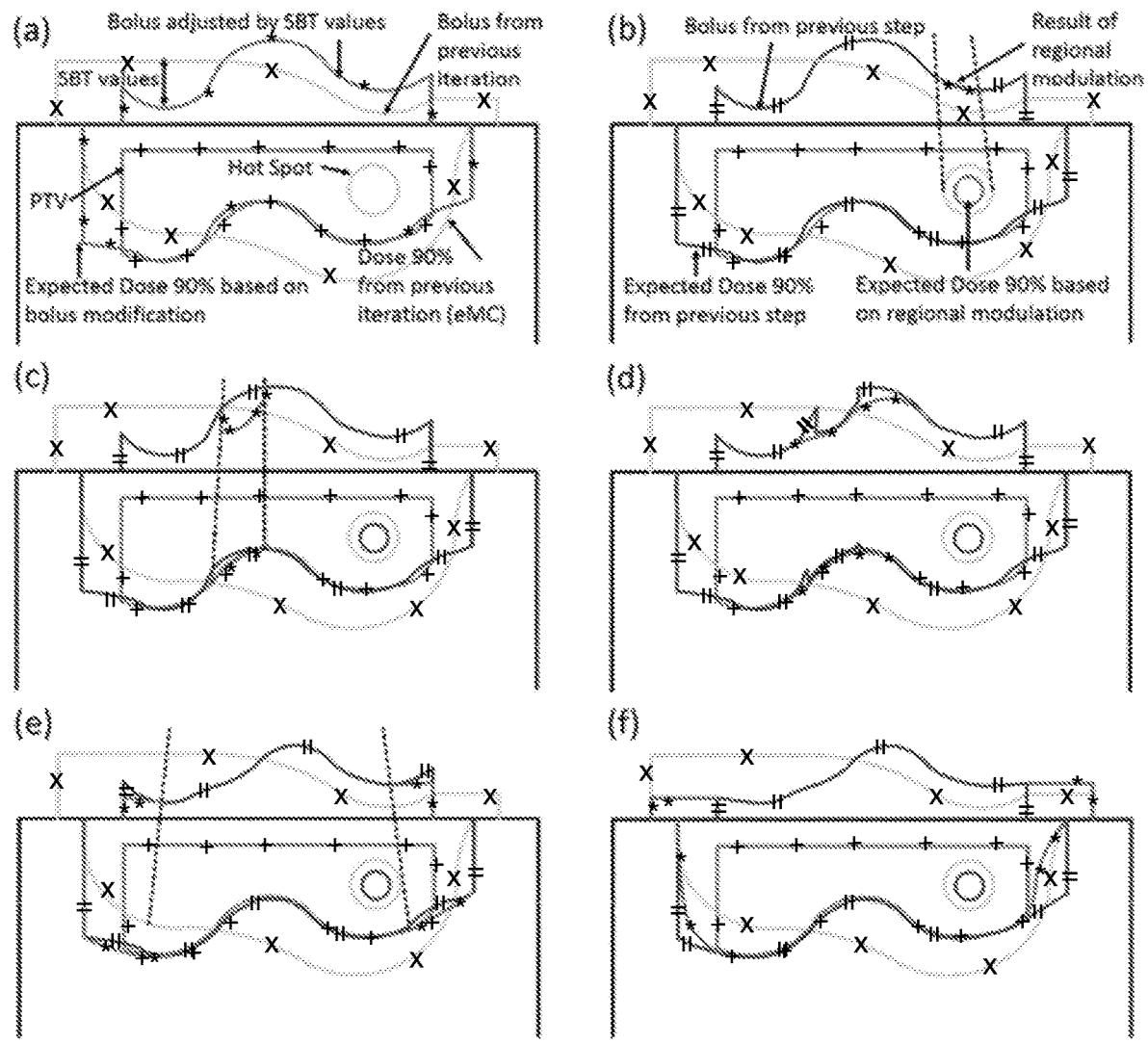
FIG. 10 illustrates an example schematic representation of bolus design algorithm after first iteration.

FIG. 10 illustrates a schematic representation of bolus design algorithm after first iteration. The lines marked with "X" indicate the previous iteration's bolus and corresponding 90% isodose line which does not yet conform well to the PTV (lines marked with "+") in this example. The lines marked with "*" show the bolus shape modified by the current step (a-f) (i.e., change in thickness by SBT value or a regional modulation operator), as well as the effect of this change on the dose distribution. For reference, lines marked with "=" denote the bolus shape and 90% isodose line from the previous step. Hot spots are indicated as circles. The individual steps are: (a) estimation of the bolus thickness based on SBT values, (b) smoothing for hot spots, (c) smoothing for dose coverage, (d) smoothing for surface irregularity, (e) adjustment at PTV margin and (f) extension outside PTV.

Figure 11:
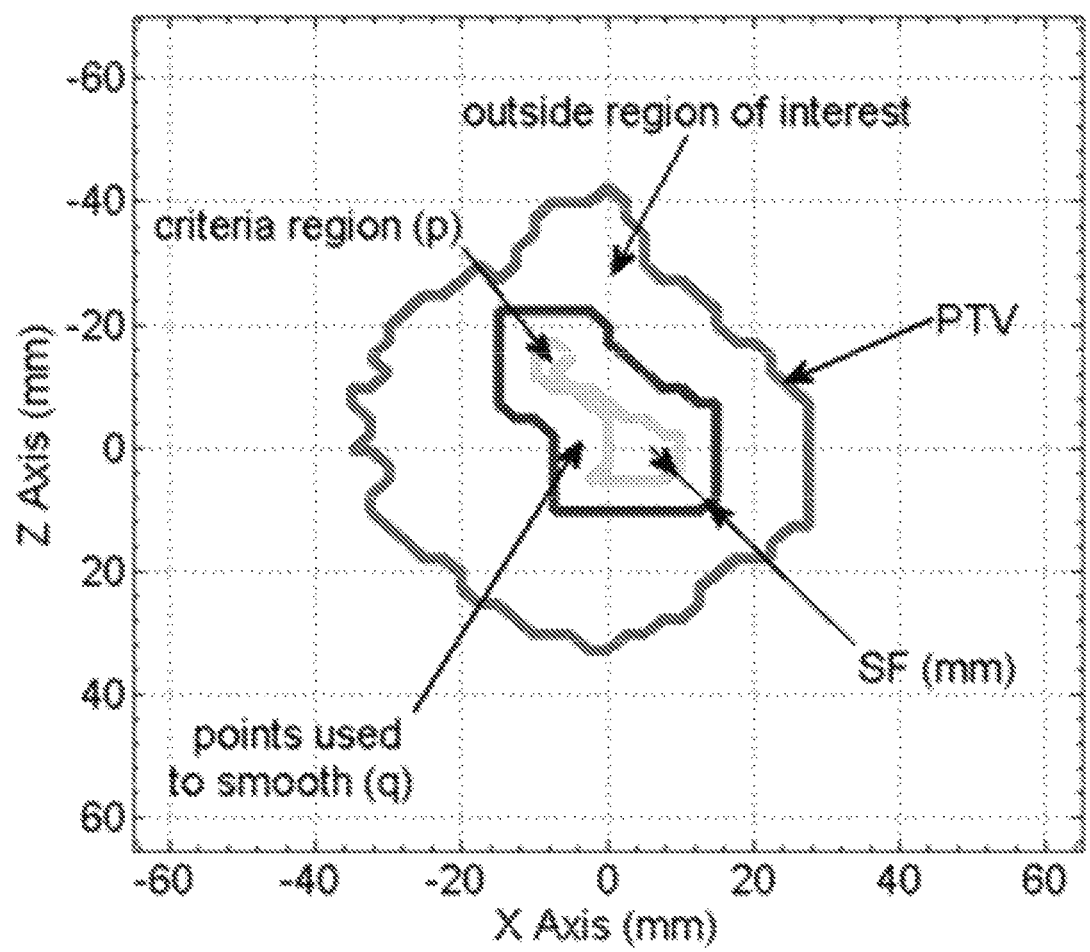
FIG. 11 is an example schematic representation of regions involved in smoothing.

Regional modulation: While the calculation of SBT values largely improves conformity of the 90% isodose surface, it does not address secondary effects, such as regional hot or cold spots or the effect of irregular bolus surface. Separate regional modulation operators are developed to address: i) hot spots in the PTV, ii) undercoverage, iii) irregular bolus surface, iv) coverage at the PTV margin, and v) extension of the bolus beyond the PTV. These operators are applied sequentially; however, we reiterate that the dose calculation is performed only by the eMC algorithm in the planning system. Three of the operators (i-iii) involve regional smoothing. In these cases, the SBT matrix is segmented into regions of interest containing points p where modulation is required, neighboring points q that are used to smooth p, and points outside of the region of interest (FIG. 11). Three smoothing operators are used according to the application:

$$SBT_p = \begin{cases} RM(p, q, SF, \text{Model}) = \dfrac{0 + \sum_{r_{pq} < SF} SBT_q \exp(-r_{pq}^2 / 2SF^2)}{1 + \sum_{r_{pq} < SF} \exp(-r_{pq}^2 / 2SF^2)} \\ \\ RM(p, q, SF, \text{Mode2}) = \dfrac{SBT_p + \sum_{r_{pq} < SF} SBT_q \exp(-r_{pq}^2 / 2SF^2)}{1 + \sum_{r_{pq} < SF} \exp(-r_{pq}^2 / 2SF^2)} \end{cases}$$

where $r_{pq}$ is the distance between p and q, and SF(mm) is the smoothing factor, controlling the width of smoothing region and smooth level (i.e., 5, 10, and 20 mm for low, medium, and high).

FIG. 11 is a schematic representation of regions involved in smoothing (e.g., to alleviate a hot spot). The red line shows the projection of the PTV onto the calculation plane. The green line denotes the region of interest satisfying the hot spot criterion and containing points, p, that will be adjusted. Points q between the blue and green lines are included in the smoothing operation, but are not adjusted.

Smoothing for hot spot: The first modulation operator aims to alleviate the hot spots that exist within the distribution after the previous iteration of eMC dose calculation (FIG. 10(b)). No smoothing is required if maximum dose is less than 110% of the prescription dose; otherwise, the hot spot region is projected to the SBT plane and smoothed. RM(Mode 1) is chosen here since the original SBT value in this criteria region may differ appreciably compared to the surroundings.

Smoothing for dose coverage: Although the calculation of SBT values aims to provide full coverage by the 90% isodose surface, accurate eMC calculation following bolus design may reveal undercoverage in certain regions of the PTV. In these regions, SBT values will be negative (i.e., to decrease bolus thickness). However, testing of the effect of SBT adjustment alone reveals that the bolus thinning must be extended somewhat beyond the region defined by the projection of the under dosed area. Accordingly, negative SBT values in the region of interest are retained, while surrounding values are smoothed (see FIG. 10(c)). RM(Mode 2) is invoked here, which will always increase target coverage since all affected points assume negative values following the operation.

Smoothing for potential irregular surface: Following the previous operations, discontinuities may be present at the boundaries of regions of interest. Surface irregularities are identified by using a gradient threshold criterion equal to two times of the mean value of gradient magnitude, and smoothed using RM(Mode 2) (FIG. 10(d)).

Adjustment at PTV margin: Relative to more central regions, the edge of the PTV receives less scattered radiation dose simply due to collimation by the electron applicator. To remedy underdosing in this region, a region of interest is defined as a 10 mm wide border inside of the projection of the PTV onto the SBT matrix (FIG. 10(e)). A function is applied to reduce bolus thickness according to:

$$SBT_p = \begin{cases} SBT_p \times (1 - KerfMA(\max(K1 - r_{pm}, 0))), & \text{if } SBT_p > 0 \\ SBT_p \times (1 + KerfMA(\max(K1 - r_{pm}, 0))), & \text{if } SBT_p < 0 \end{cases}$$

where values are adjusted along radial lines from the central axis: m exists on the inner boundary of the region of interest, p exists within the region of interest, $r_{pm}$ is the distance between p and m, $$KerfMA(x) = \exp\left(-\frac{x^2}{2\,sigma^2}\right) \text{ and } K1 = \sqrt{-2\ln(0.01)\,sigma^2}$$

Figure 12:
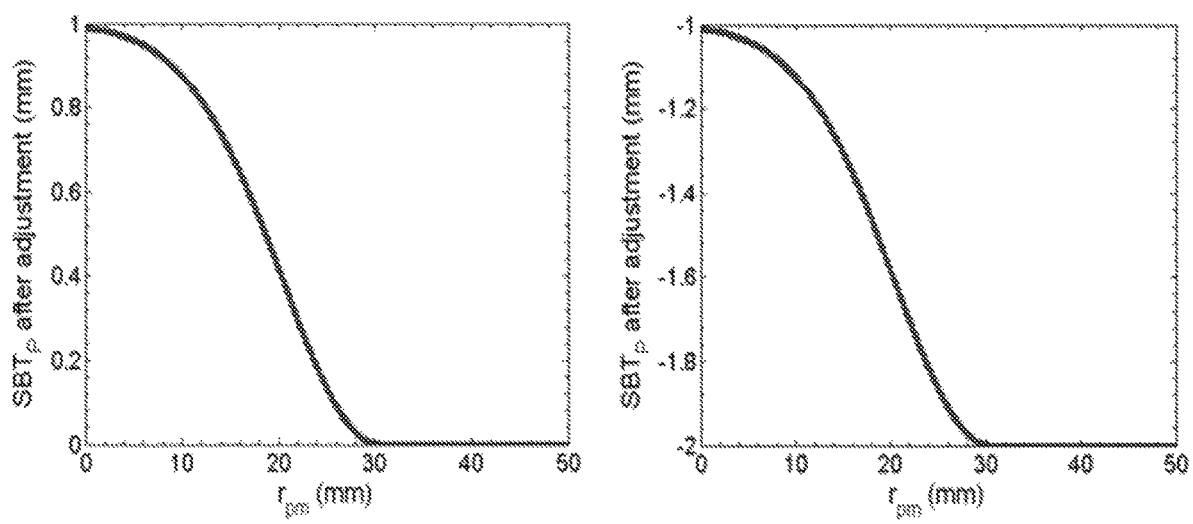
FIG. 12 illustrates a graph of a ratio used in the calculation for adjusting the bolus design.

(i.e., the distance over which KerfMA(x) increases from 0.01 to 1 (FIG. 12)). In practice, we determine that effective values of sigma must be related to beam profile, increasing with both energy and applicator dimension. In this work and for coding simplicity, an approximation of $$sigma = \sqrt{Energy \times Applicator)}$$

is employed.

Shift outside PTV: The area corresponding to all ray lines between the edge of the PTV and a distance 1.0 cm beyond the electron aperture are subject to this operator. In this region, bolus thicknesses are simply extruded:

$$SBT_p = SBT_n$$

where n is the intersection of PTV contour and line from p to the projection of central axis (FIG. 10(f)).

Figure 3A:
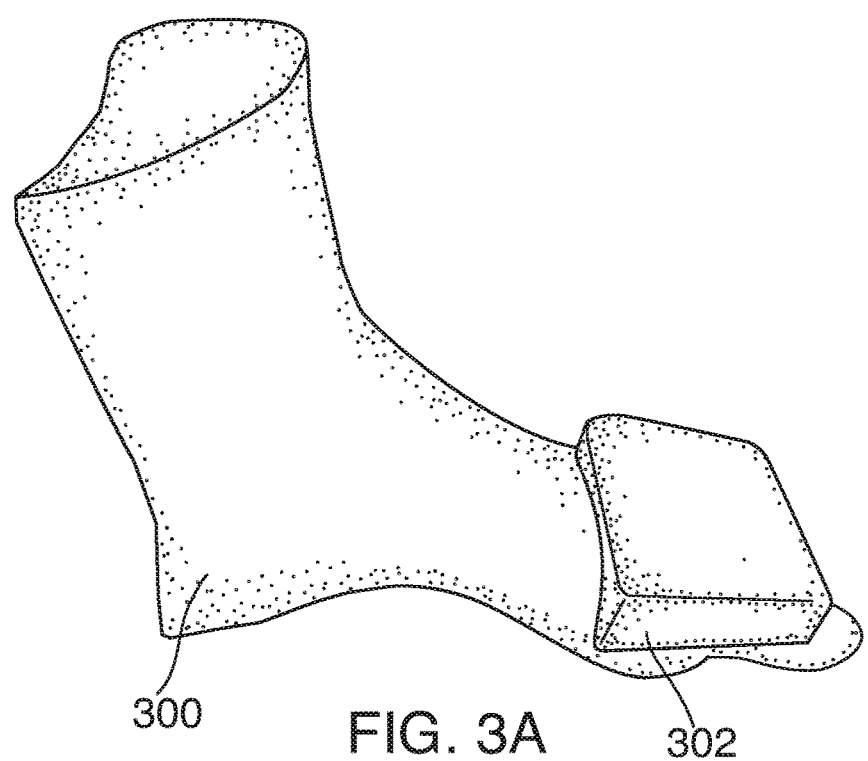
FIG. 3A illustrates an example of a 3D printed bolus.
Figure 3B:
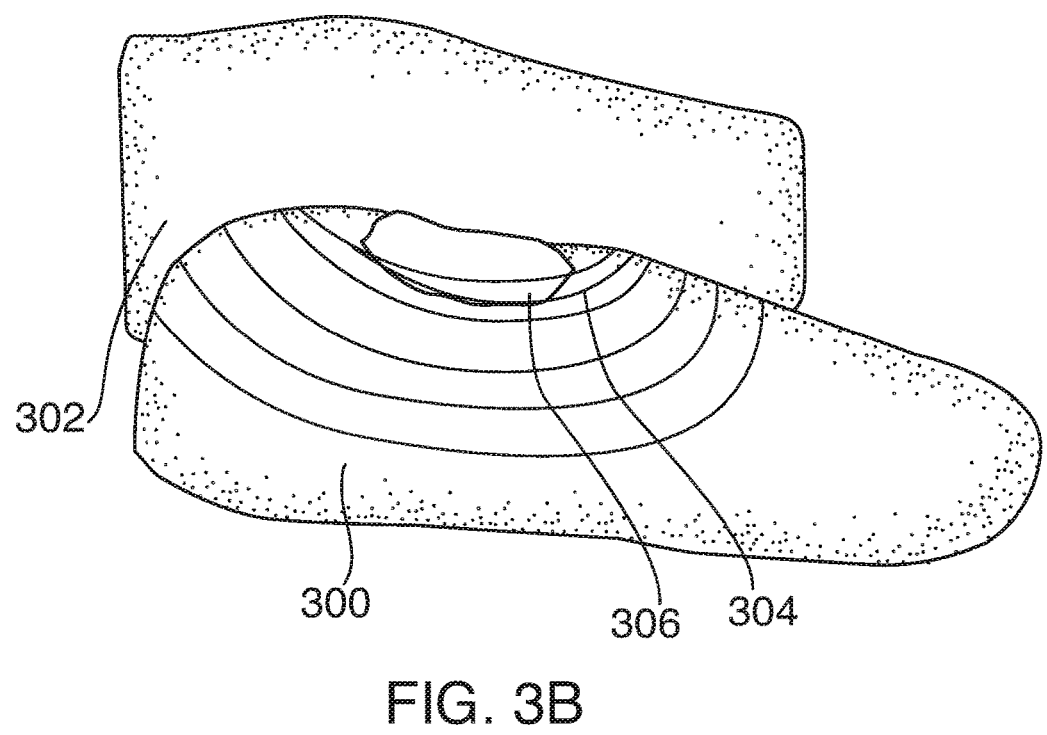
FIG. 3B illustrates a cutaway view of the 3D printed bolus and calculated dose distribution within a patient foot.

FIG. 3A illustrates an example of a 3D printed bolus 302 in place on a cast of a foot 300. FIG. 3B illustrates a cutaway view of the 3D printed bolus 302 and calculated dose distribution within a patient foot 300. The PTV 306 is within a region 306 that receives the prescribed level of the administered radiotherapy dose, thereby focusing the radiotherapy and reducing its effects on other surrounding tissue. While this example shows for a bolus use with a foot, the system can receive CT scan data of virtually any body part, and design a corresponding bolus for 3D printing based on that CT scan data, a desired treatment region, and a desired radiation therapy dose.

Figure 4:
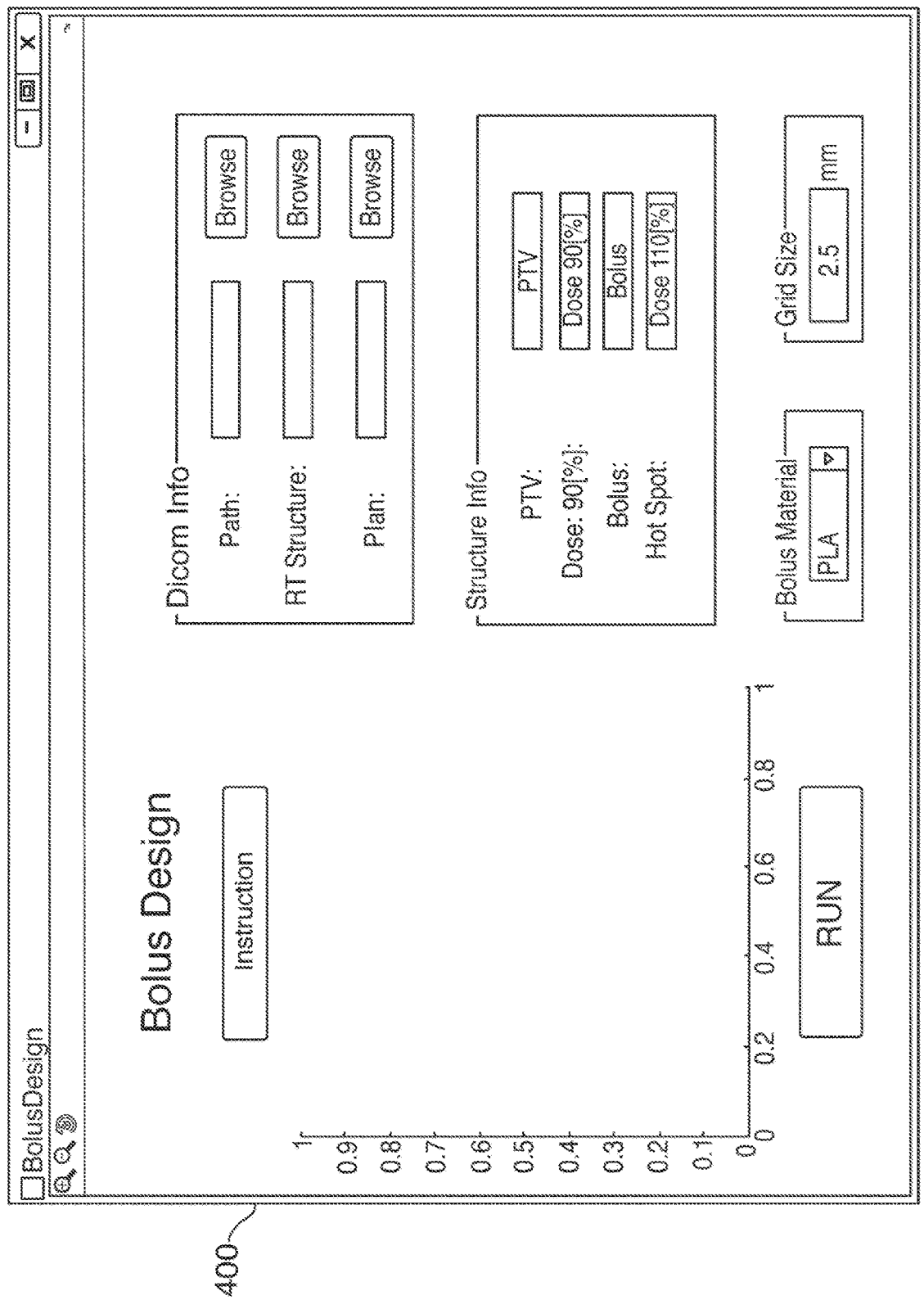
FIG. 4 illustrates an example user interface for bolus design in an initial, pre-design stage.

FIG. 4 illustrates an example user interface 400 for bolus design in an initial, pre-design stage. In this example, the user selects a bolus material, such as PLA, and the system uses the radiation characteristics of that material when calculating the size and shape of the 3D-printed bolus. The user also specifies other data, such as the CT scan data of the patient, the desired treatment region within the CT scan data, a desired radiation treatment regime and dosage information, and so forth. The CT scan data can be in DICOM format, for example. The structure set as delineated on the CT scan data in the treatment planning system can be represented in DICOM RT Structure format or other suitable digital format. The PTV structure defines within the structure set to which the dose must conform. The initial bolus object (if any) can be selected from a set as defined in the treatment planning system, such as a selection from a template set of bolus shapes. The level of a hot-spot within the dose distribution indicates a level of compensation that should be performed during optimization. The user interface also allows the user to specify the bolus material, such as PLA, ABS, or other material. The user interface allows the user to specify a resolution or grid size to be used in the bolus optimization process. Using this data as input, the user can then click the "RUN" button to initiate a bolus design.

Figure 5:
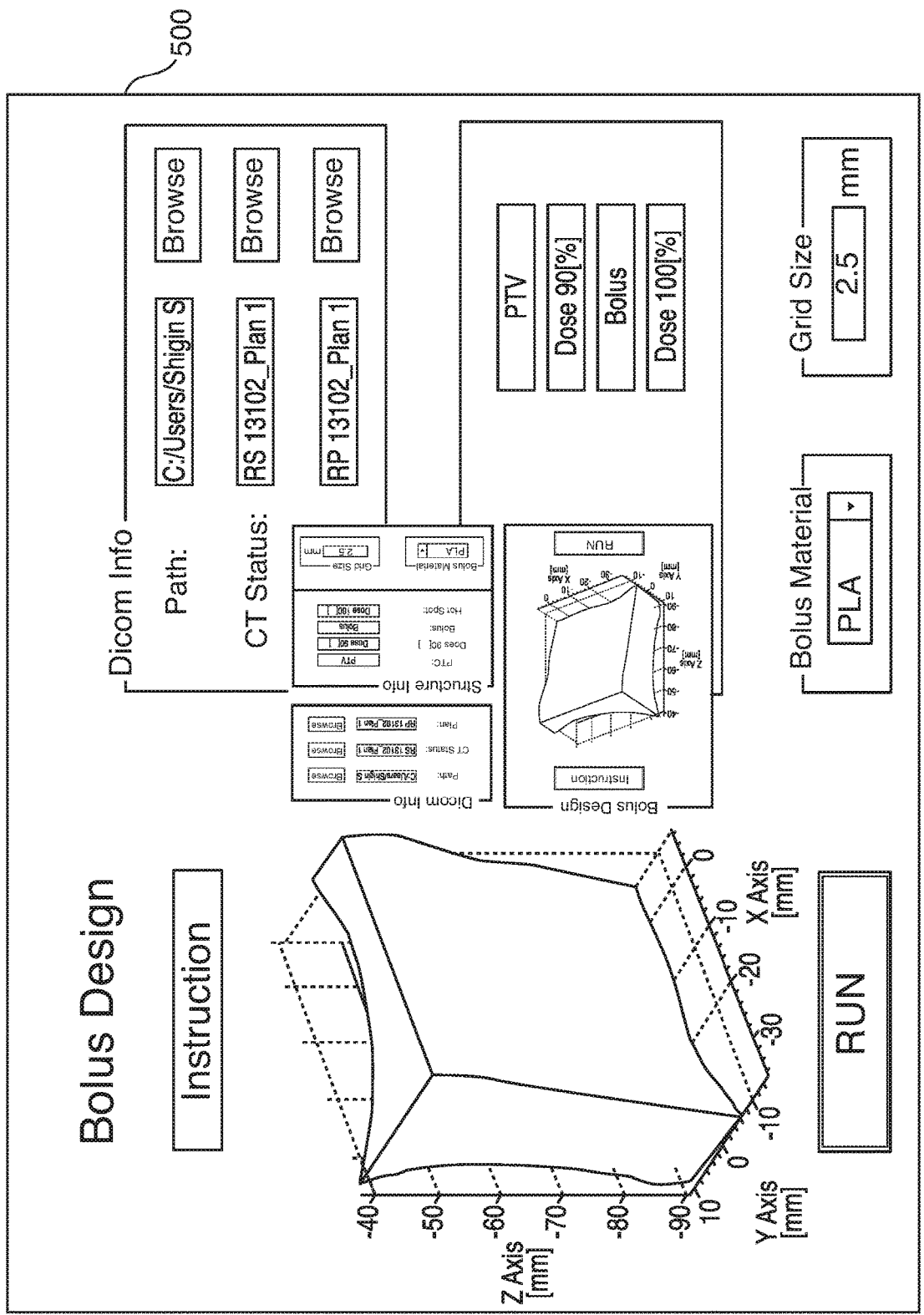
FIG. 5 illustrates the example user interface for bolus design during design.

FIG. 5 illustrates the example user interface 500 after the user clicks the "RUN" button. The user interface 500 can present a virtual 3D model of the bolus on the display prior to printing the 3D model. The user interface 500 allows the user to continue to tweak the various settings, such as the bolus material, and iteratively view what the 3D-printed bolus will look like with updated settings. The system can provide additional details about the bolus to be 3D printed, such as estimated weight, dimensions, time to produce, materials cost and quantity, maximum number (if any) of treatments the 3D-printed bolus is rated for, and so forth. When the user is satisfied with the view of the design on the user interface 500, the user can output the bolus model to a 3D printer to be created.

Certain radiation treatments are directed to sensitive parts of the body, such as radiation therapy for breast cancer. Breast tissue is deformable and can change position and shape more than body parts with bones to support and give structure. Thus, a bolus for use with radiation therapy for breast cancer treatments may be difficult to position. Further, certain portions of the affected region of the body, such as skin on the inframammary fold, may become irritated or have other issues stemming from radiation treatment. To address these and other issues, the system can analyze CT scan data of the breast, and 3D print an immobilization support to stabilize the breast. Additionally, a custom 3D-printed bolus, as described above, can be incorporated into the immobilization support.

Figure 6:
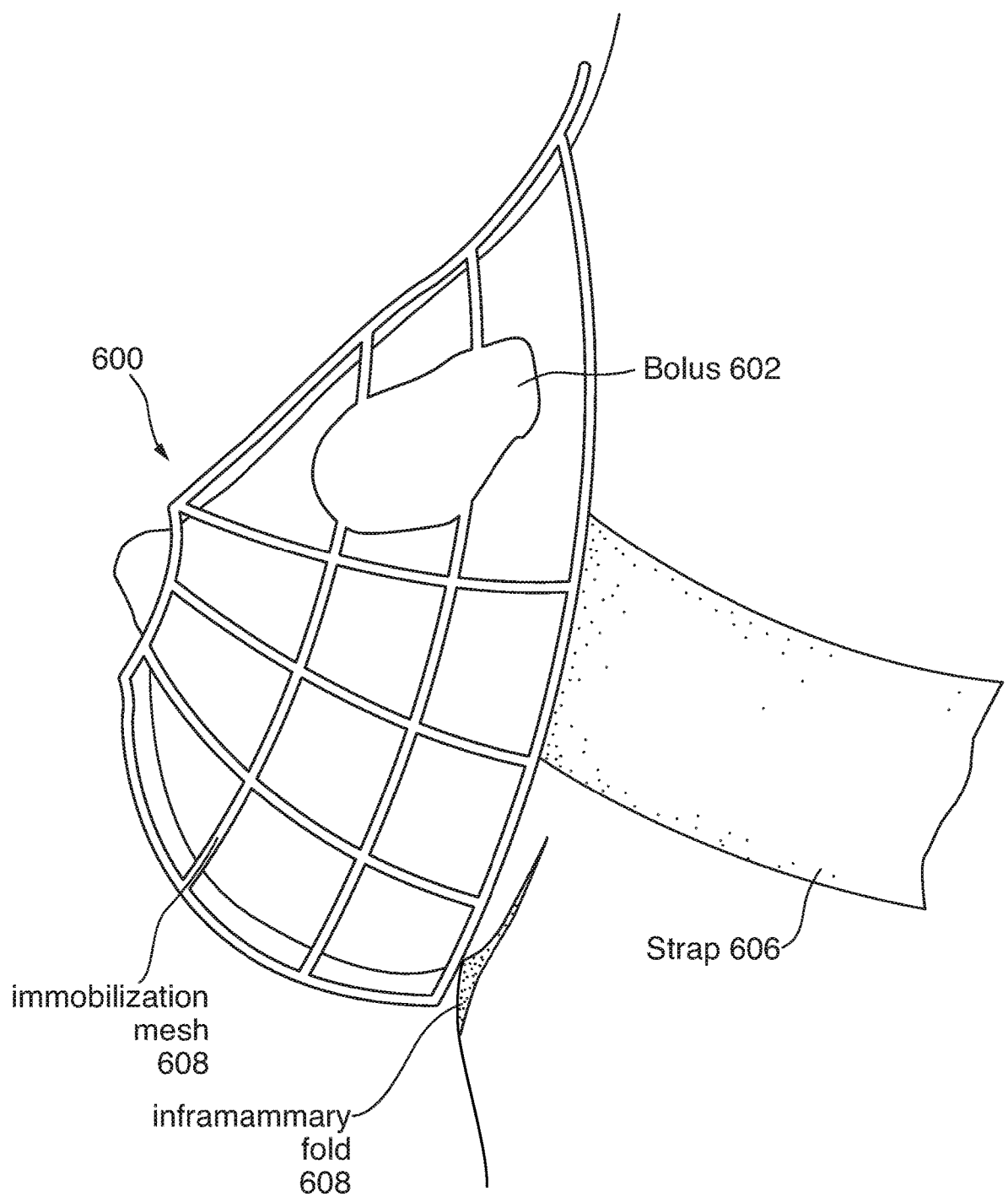
FIG. 6 illustrates an example immobilization support with an integrated bolus.

FIG. 6 illustrates an example immobilization support 600 with an integrated bolus 602. The immobilization support 600 is, in this example, an immobilization mesh 604 with a strap 606 that goes around the patient's torso to hold the immobilization mesh 604 in place. A bolus 602 is integrated into the immobilization mesh 604. The bolus 602 is not a separate part attached or affixed to the immobilization mesh 604, but rather the bolus 602 and the immobilization mesh 604 are created as part of the same 3D printing process. The immobilization mesh 604 can be a mesh, a solid container, a substantially solid container, a block with a cavity in to which the breast (or other body part) is inserted as part of treatment, and so forth. The mesh 604 is shown here as one example. Because the immobilization mesh 604 is generated based on CT scan data, the immobilization mesh 604 fits the dimensions of the patient in a very precise manner. In this way, when the patient wears the immobilization support 600, the patient's breast is supported to avoid damage or irritation to the inframammary fold 608, and the breast tissue is immobilized so the bolus is in the same position for each treatment session in a periodic treatment regime. Thus, the radiation treatment is administered consistently to the same region of the breast in a manner that accurately reflects the dose distribution created during treatment planning. The breast is immobilized into the same position, and the bolus is in the same position relative to the immobilized breast. The integrated immobilization mesh 604 and bolus 602 allows only minimal dose build up over area of immobilization, i.e. the area of the mesh 604 other than the bolus 602. The bolus 602 is designed in a patient-specific way to enable precise and consistent radiation treatment for that patient's body. Further, this approach can reduce labor requirements associated with designing, fitting, and placing the bolus as part of a radiation therapy regime. The bolus 602 on the immobilization support 600 can be designed for any of the three different types of radiation outlined above: photon, electron, and proton. While the example provided herein relates to breast tissue, a similar approach with an immobilization mesh 604 and integrated 3D-printed bolus 602 can be applied to virtually any other body parts, such as head and neck, scalp, ankles, and other extremities.

The system can, when designing such a 3D-printed immobilization support 600 and integrated bolus 602, reduce of build-up effect outside of the bolus area. The system can control various aspects of the immobilization mesh 604, such as the mesh density or size of cells in the mesh, the thickness of the 'lines' of 3D-printed material in the mesh, or effective electron density of the 3D-printed material (sometimes called 'infill' in 3D printing terminology). In one variation, the immobilization support 600 can be 3D printed to include brackets or grommets or some other attachment for connecting the strap 606.

In a progressively changing radiation treatment, the system can receive CT scan data (or other body imaging data) of the patient, and design a series of immobilization meshes 604 and boluses 602 for different stages of the treatment plan. For example, the treatment plan may include a high dose of electron radiation for weeks 1 and 2, while the electron radiation dose is lowered for weeks 3 and 4. The system can design, and 3D-print on-demand (such as the night before an appointment at which a new bolus is required), a first combination immobilization mesh 604 and bolus 602 for weeks 1 and 2, and a second combination immobilization mesh 604 and bolus 602 for weeks 3 and 4. Each combination is based on the same patient CT scan data, but incorporates a bolus 602 of a different shape, size, type, and/or in a different position on the immobilization mesh 604. Additionally, the system can incorporate feedback from the treatment progress and revise yet-unprinted ones in the series to be tailored for the changing radiation therapy needs and the body's changing reactions to the radiation therapy.

When applying radiation therapy, doctors (or others) often wish to know whether the radiation is being administered properly, and how much radiation is being administered, among other data points. A 3D-printed bolus can include several mechanisms for collecting this data. For example, a 3D-printed bolus can be designed so that the 3D printing process creates (or leaves) a specific cavity or cavities in the bolus for receiving radiation dosimeters. A doctor or other user can insert a radiation dosimeter into the cavity in the bolus prior to treatment to gather data during treatment, then can remove the radiation dosimeter after treatment. The shape of the cavity can be tailored for a specific kind of dosimeter, so only the correct type of dosimeter(s) will fit. The cavity can be virtually any shape, and can optionally include latches, brackets, or other restraining mechanism to position the dosimeter and retain it in place. Because the 3D design and printing process allows full control of the 3D design of the bolus, dosimeters can be embedded within the bolus to enable in vivo dosimetry. Example dosimeters include ionization chambers, diodes, metal-oxide-semiconductor field-effect transistors (MOSFETs), radiographic film, radiochromic film, diamond detectors, optically stimulated luminescence dosimeters (OSLDs), or arrays thereof. Because the bolus is in direct contact with the skin, the dosimeters can also be placed proximal to the skin surface (or very close to the skin surface within or on the bolus) to allow real-time readout of the radiation dose received by the skin during treatment.

In one embodiment, the material making up the bolus can itself be a sort of dosimeter. Certain materials are scintillators, or materials which exhibit scintillation, the property of luminescence when excited by ionizing radiation, such as PET or PEN plastics that are 3D-printable. Scintillators can be organic crystals or liquids, inorganic crystals, specialized glass, as well as plastic scintillators. Plastic scintillators typically include a scintillator (or fluor) suspended in a polymer base. As the 3D printer creates the bolus, all the material from which the bolus is created can include one or more scintillator materials. Then, as the bolus is used in the radiation therapy, the scintillators react and fluoresce. The bolus can include different kinds of scintillators triggered at different radiation levels. Thus, the type, amount, or position of scintillator reacting can provide an indication of the quantity and location of the administered radiation. The 3D printer can also incorporate different scintillators in different regions of the bolus. The 3D printer can incorporate scintillators in the bolus in patterns that form words or symbols when a suitable radiation dose is applied to the bolus. For example, the majority of the bolus material is a non-scintillator, and during 3D printing, certain regions of the bolus are constructed with scintillator materials in patterns that fluoresce when exposed to a specific amount of radiation. Then, when the bolus is used for treatment, the patterns of scintillator materials embedded in the bolus fluoresce. In one example, a pattern of scintillator material in the shape of a smiley face, a checkmark, or the word "YES" can fluoresce when the radiation is at a desired level. Conversely, patterns of scintillator materials embedded in the bolus can also indicate when the dose is too low or too high with different patterns, such as a letter "X" or a frowny face. With respect to the immobilization mesh 604, the 3D printer can also include scintillators in the immobilization mesh 604 to provide a visual indication of whether the dose of radiation is insufficient or is too high.

While the primary embodiment discussed herein is a bolus that is in direct contact with the skin of a patient, similar 3D-printing approaches and algorithms can be adapted for other, related uses that custom adapt a radiation dose for a patient but that are not in direct contact with the skin of the patient. For example, instead of an algorithm for shaping a bolus to be applied to a patient's skin in order to deliver a desired radiation dose, a similar design process and similar algorithm can be applied to design a custom proton compensator to be positioned upstream in a proton radiation beam. Such a proton compensator would not be in direct contact with the patient's skin, but would be upstream. When in position for the proton radiation beam, the custom, patient-specific proton compensator modulates the depth of the high dose deposited as a function of position across the beam so that the desired amount of proton radiation is delivered and that the therapeutic dose distribution conforms to the curvature of the deep aspect of the tumor volume. Radiation treatment can include a combination of a proton compensator upstream and a bolus in contact with the patient's skin.

Figure 7:
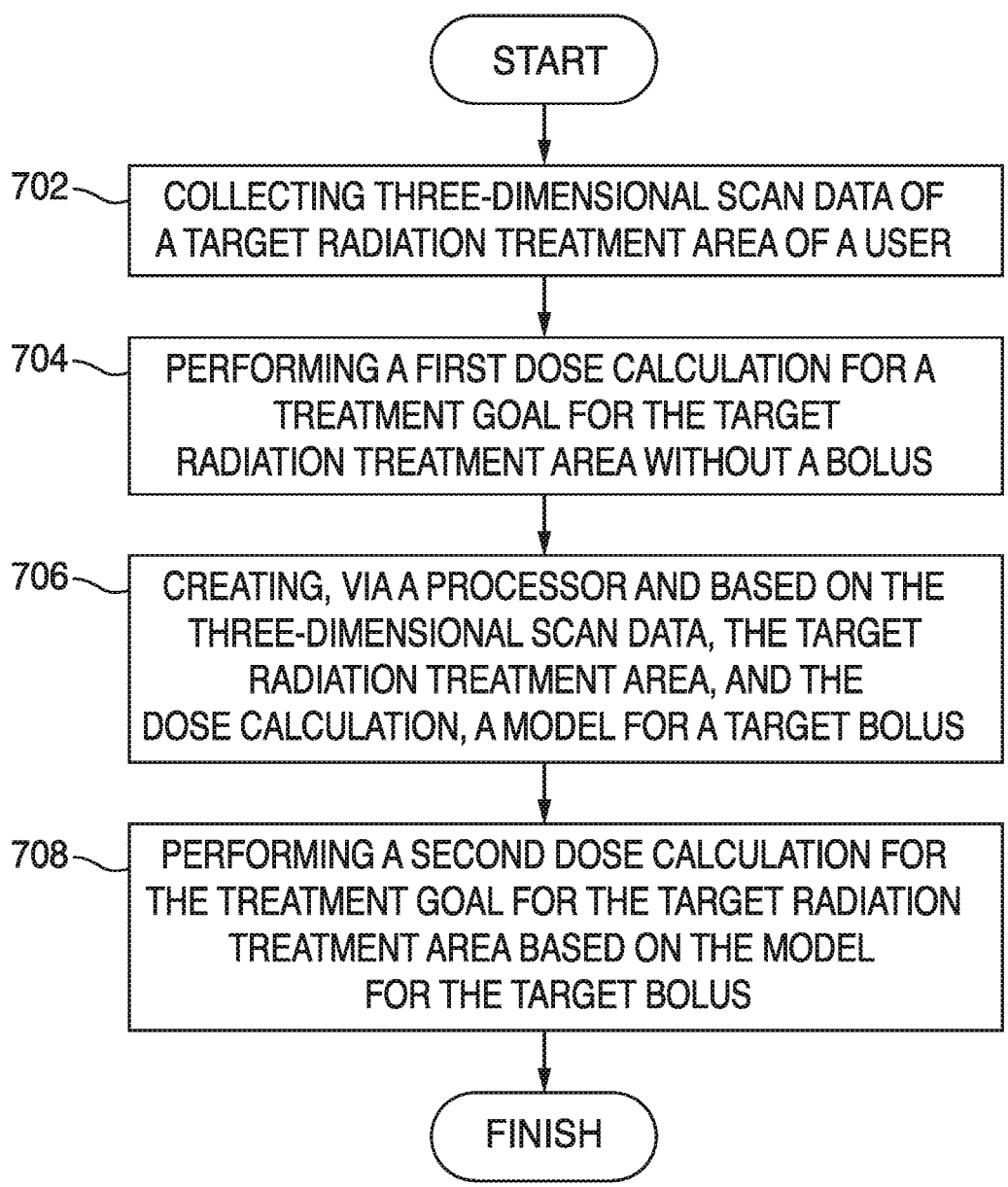
FIG. 7 illustrates an example method embodiment.

FIG. 7 illustrates an example method embodiment. The operations presented herein are examples. The method embodiment can include additional steps, remove certain steps, perform the steps in different orders than what is presented herein, and can perform the steps in any combination or permutation. A system configured to practice the example method collects three-dimensional scan data of a target radiation treatment area of a user (702). The system performs a first dose calculation for a treatment goal for the target radiation treatment area without a bolus (704). The dose calculations can be based on an electron Monte Carlo (eMC) algorithm. The system creates, based on the three-dimensional scan data, the target radiation treatment area, and the dose calculation, a model for a target bolus (706).

The system performs a second dose calculation for the treatment goal for the target radiation treatment area based on the model for the target bolus (708). When the second dose calculation satisfies conditions associated with the treatment goal, the system can output the model for the target bolus to a fabrication device to produce a replica of the target bolus for use with the target radiation treatment area of the user. If the second dose calculation does not satisfy the conditions associated with the treatment goal, the system can perform an analysis of the model for the target bolus for at least one of a hot spot, a cool spot, dose coverage, surface irregularity, a margin of a planning target volume, or conformity at edges of the planning target volume. Based on the analysis, the system can revise the model to yield a revised model, and output the revised model to the fabrication device to produce the replica of the target bolus for use with the target radiation treatment area of the user. The replica can be made up of polylactic acid, or some other material suitable for use with a 3D printer. The system can iterate the analysis and revising the model until the revised model satisfies the conditions associated with the treatment goal. The fabrication device can be a 3D printer. The model can be an STL file. The system can present or render the model in a user interface prior to fabrication via the 3D printer.

After the bolus is 3D printed, the system can verify that it satisfies the conditions associated with the treatment goal based on a computed tomography scan of the bolus while placed on the target radiation treatment area of the user. The system can similarly gather radiation data via dosimeters embedded in the bolus, inserted into the bolus, or via scintillators that are part of the bolus material.

The patient-facing side of the bolus is shaped to conform to a surface of the target radiation treatment area. The beam-incident side of the replica can be shaped to a regular geometric surface or to some other shape or contour such that radiation passed through the bolus is delivered in a desired dosage to a desired portion of the skin or body of the user when placed on the target radiation treatment area of the user and a radiation beam is applied to the target radiation treatment area of the user through the bolus. The bolus can be reusable for multiple radiation treatment sessions.

Various embodiments of the disclosure are described in detail herein. While specific implementations are described, it should be understood that this is done for illustration purposes only. Other components and configurations may be used without parting from the spirit and scope of the disclosure.

Figure 8:
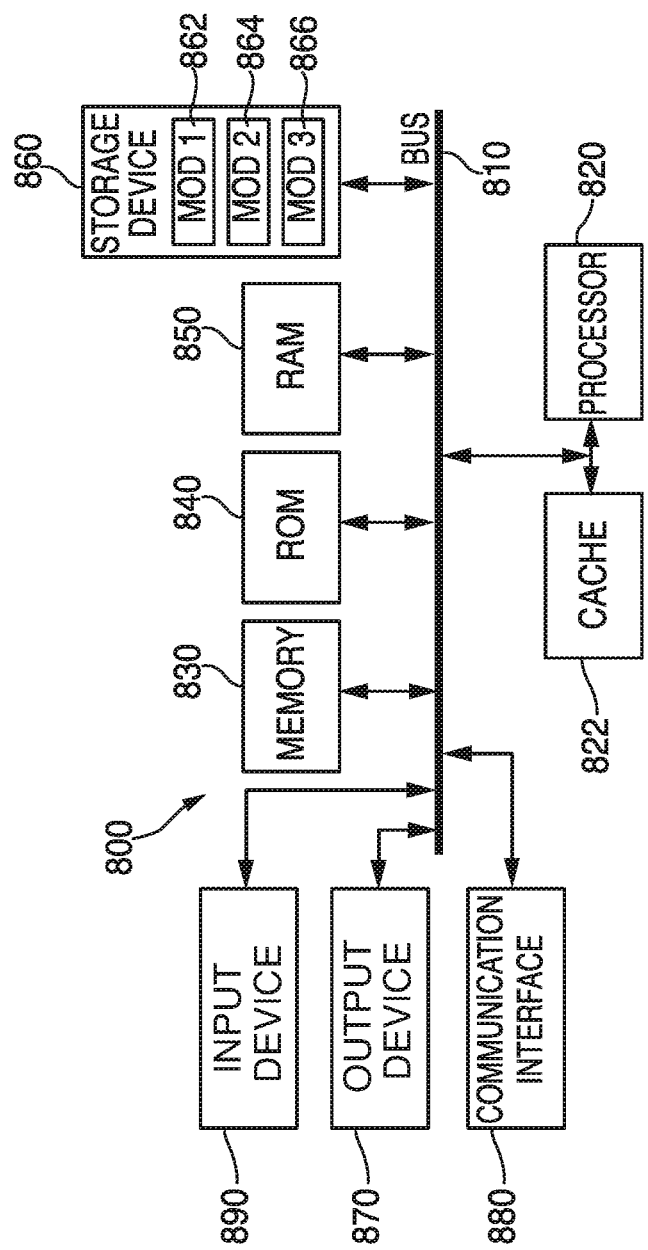
FIG. 8 illustrates an example system embodiment.

With reference to FIG. 8, an exemplary system and/or computing device 800 includes a processing unit (CPU or processor) 820 and a system bus 810 that couples various system components including the system memory 830 such as read only memory (ROM) 840 and random access memory (RAM) 850 to the processor 820. The system 800 can include a cache 822 of high-speed memory connected directly with, in close proximity to, or integrated as part of the processor 820. The system 800 copies data from the memory 830 and/or the storage device 860 to the cache 822 for quick access by the processor 820. In this way, the cache provides a performance boost that avoids processor 820 delays while waiting for data. These and other modules can control or be configured to control the processor 820 to perform various operations or actions. Other system memory 830 may be available for use as well. The memory 830 can include multiple different types of memory with different performance characteristics. It can be appreciated that the disclosure may operate on a computing device 800 with more than one processor 820 or on a group or cluster of computing devices networked together to provide greater processing capability. The processor 820 can include any general purpose processor and a hardware module or software module, such as module 1 862, module 2 864, and module 3 866 stored in storage device 860, configured to control the processor 820 as well as a special-purpose processor where software instructions are incorporated into the processor. The processor 820 may be a self-contained computing system, containing multiple cores or processors, a bus, memory controller, cache, etc. A multi-core processor may be symmetric or asymmetric. The processor 820 can include multiple processors, such as a system having multiple, physically separate processors in different sockets, or a system having multiple processor cores on a single physical chip. Similarly, the processor 820 can include multiple distributed processors located in multiple separate computing devices, but working together such as via a communications network. Multiple processors or processor cores can share resources such as memory 830 or the cache 822, or can operate using independent resources. The processor 820 can include one or more of a state machine, an application specific integrated circuit (ASIC), or a programmable gate array (PGA) including a field PGA.

The system bus 810 may be any of several types of bus structures including a memory bus or memory controller, a peripheral bus, and a local bus using any of a variety of bus architectures. A basic input/output (BIOS) stored in ROM 840 or the like, may provide the basic routine that helps to transfer information between elements within the computing device 800, such as during start-up. The computing device 800 further includes storage devices 860 or computer-readable storage media such as a hard disk drive, a magnetic disk drive, an optical disk drive, tape drive, solid-state drive, RANI drive, removable storage devices, a redundant array of inexpensive disks (RAID), hybrid storage device, or the like. The storage device 860 can include software modules 862, 864, 866 for controlling the processor 820. The system 800 can include other hardware or software modules. The storage device 860 is connected to the system bus 810 by a drive interface. The drives and the associated computer-readable storage devices provide nonvolatile storage of computer-readable instructions, data structures, program modules and other data for the computing device 800. In one aspect, a hardware module that performs a particular function includes the software component stored in a tangible computer-readable storage device in connection with the necessary hardware components, such as the processor 820, bus 810, display 870, and so forth, to carry out a particular function. In another aspect, the system can use a processor and computer-readable storage device to store instructions which, when executed by the processor, cause the processor to perform operations, a method or other specific actions. The basic components and appropriate variations can be modified depending on the type of device, such as whether the device 800 is a small, handheld computing device, a desktop computer, or a computer server. When the processor 820 executes instructions to perform "operations", the processor 820 can perform the operations directly and/or facilitate, direct, or cooperate with another device or component to perform the operations.

Although the exemplary embodiment(s) described herein employs the hard disk 860, other types of computer-readable storage devices which can store data that are accessible by a computer, such as magnetic cassettes, flash memory cards, digital versatile disks (DVDs), cartridges, random access memories (RAMs) 850, read only memory (ROM) 840, a cable containing a bit stream and the like, may also be used in the exemplary operating environment. Tangible computer-readable storage media, computer-readable storage devices, or computer-readable memory devices, expressly exclude media such as transitory waves, energy, carrier signals, electromagnetic waves, and signals per se.

To enable user interaction with the computing device 800, an input device 890 represents any number of input mechanisms, such as a microphone for speech, a touch-sensitive screen for gesture or graphical input, keyboard, mouse, motion input, speech and so forth. An output device 870 can also be one or more of a number of output mechanisms known to those of skill in the art. In some instances, multimodal systems enable a user to provide multiple types of input to communicate with the computing device 800. The communications interface 880 generally governs and manages the user input and system output. There is no restriction on operating on any particular hardware arrangement and therefore the basic hardware depicted may easily be substituted for improved hardware or firmware arrangements as they are developed.

For clarity of explanation, the illustrative system embodiment is presented as including individual functional blocks including functional blocks labeled as a "processor" or processor 820. The functions these blocks represent may be provided through the use of either shared or dedicated hardware, including, but not limited to, hardware capable of executing software and hardware, such as a processor 820, that is purpose-built to operate as an equivalent to software executing on a general purpose processor. For example the functions of one or more processors presented in FIG. 8 may be provided by a single shared processor or multiple processors. (Use of the term "processor" should not be construed to refer exclusively to hardware capable of executing software.) Illustrative embodiments may include microprocessor and/or digital signal processor (DSP) hardware, read-only memory (ROM) 840 for storing software performing the operations described below, and random access memory (RAM) 850 for storing results. Very large scale integration (VLSI) hardware embodiments, as well as custom VLSI circuitry in combination with a general purpose DSP circuit, may also be provided.

The logical operations of the various embodiments are implemented as: (1) a sequence of computer implemented steps, operations, or procedures running on a programmable circuit within a general use computer, (2) a sequence of computer implemented steps, operations, or procedures running on a specific-use programmable circuit; and/or (3) interconnected machine modules or program engines within the programmable circuits. The system 800 shown in FIG. 8 can practice all or part of the recited methods, can be a part of the recited systems, and/or can operate according to instructions in the recited tangible computer-readable storage devices. Such logical operations can be implemented as modules configured to control the processor 820 to perform particular functions according to the programming of the module. For example, FIG. 8 illustrates three modules Mod1 862, Mod2 864 and Mod3 866 which are modules configured to control the processor 820. These modules may be stored on the storage device 860 and loaded into RAM 850 or memory 830 at runtime or may be stored in other computer-readable memory locations.

One or more parts of the example computing device 800, up to and including the entire computing device 800, can be virtualized. For example, a virtual processor can be a software object that executes according to a particular instruction set, even when a physical processor of the same type as the virtual processor is unavailable. A virtualization layer or a virtual "host" can enable virtualized components of one or more different computing devices or device types by translating virtualized operations to actual operations. Ultimately however, virtualized hardware of every type is implemented or executed by some underlying physical hardware. Thus, a virtualization compute layer can operate on top of a physical compute layer. The virtualization compute layer can include one or more of a virtual machine, an overlay network, a hypervisor, virtual switching, and any other virtualization application.

The processor 820 can include all types of processors disclosed herein, including a virtual processor. However, when referring to a virtual processor, the processor 820 includes the software components associated with executing the virtual processor in a virtualization layer and underlying hardware necessary to execute the virtualization layer. The system 800 can include a physical or virtual processor 820 that receive instructions stored in a computer-readable storage device, which cause the processor 820 to perform certain operations. When referring to a virtual processor 820, the system also includes the underlying physical hardware executing the virtual processor 820.

Embodiments within the scope of the present disclosure may also include tangible and/or non-transitory computer-readable storage devices for carrying or having computer-executable instructions or data structures stored thereon. Such tangible computer-readable storage devices can be any available device that can be accessed by a general purpose or special purpose computer, including the functional design of any special purpose processor as described above. By way of example, and not limitation, such tangible computer-readable devices can include RAM, ROM, EEPROM, CD-ROM or other optical disk storage, magnetic disk storage or other magnetic storage devices, or any other device which can be used to carry or store desired program code in the form of computer-executable instructions, data structures, or processor chip design. When information or instructions are provided via a network or another communications connection (either hardwired, wireless, or combination thereof) to a computer, the computer properly views the connection as a computer-readable medium. Thus, any such connection is properly termed a computer-readable medium. Combinations of the above should also be included within the scope of the computer-readable storage devices.

Computer-executable instructions include, for example, instructions and data which cause a general purpose computer, special purpose computer, or special purpose processing device to perform a certain function or group of functions. Computer-executable instructions also include program modules that are executed by computers in stand-alone or network environments. Generally, program modules include routines, programs, components, data structures, objects, and the functions inherent in the design of special-purpose processors, etc. that perform particular tasks or implement particular abstract data types. Computer-executable instructions, associated data structures, and program modules represent examples of the program code means for executing steps of the methods disclosed herein. The particular sequence of such executable instructions or associated data structures represents examples of corresponding acts for implementing the functions described in such steps.

Other embodiments of the disclosure may be practiced in network computing environments with many types of computer system configurations, including personal computers, hand-held devices, multi-processor systems, microprocessor-based or programmable consumer electronics, network PCs, minicomputers, mainframe computers, and the like. Embodiments may also be practiced in distributed computing environments where tasks are performed by local and remote processing devices that are linked (either by hard-wired links, wireless links, or by a combination thereof) through a communications network. In a distributed computing environment, program modules may be located in both local and remote memory storage devices.

The various embodiments described above are provided by way of illustration only and should not be construed to limit the scope of the disclosure. For example, the principles herein can be applied to any clinical case involving electron beam therapy. The 3D printing process can also apply to x-ray photon beam therapy over multiple sites where the tumor volume is superficial, although the design process for the bolus may be modified somewhat for photons. The bolus design algorithm can be changed, for example, to support photon or proton transport instead of electron transport. The eMC algorithm in 202, 206, and 214 can be replaced by a megavoltage photon dose calculation algorithm. Various modifications and changes may be made to the principles described herein without following the example embodiments and applications illustrated and described herein, and without departing from the spirit and scope of the disclosure. Claim language reciting "at least one of" a set indicates that one member of the set or multiple members of the set satisfy the claim.

The invention claimed is:

1. An apparatus for controlling a dose delivered to a patient during radiation therapy, the apparatus comprising:
a patient-specific radiation bolus having an inner patient-facing surface and an outer beam-incident surface;
said inner patient-facing surface being configured to conform to a surface of the patient;
said outer beam-incident surface being shaped to spatially modulate the dose delivered to the patient when said inner patient-facing surface is placed against the patient and radiation is transmitted through said patient-specific radiation bolus during a radiation therapy procedure;
said patient-specific radiation bolus having formed therein a dosimeter cavity configured for removable insertion of a radiation dosimeter for performing in-vivo dosimetry during the radiation therapy procedure, such that the radiation dosimeter is removable from said dosimeter cavity after the radiation therapy procedure, said dosimeter cavity being located such that when the radiation dosimeter is inserted into said patient-specific radiation bolus and said patient-specific radiation bolus is contacted with the patient, the radiation dosimeter resides proximal to the surface of the patient.

2. The apparatus according to claim 1 wherein said dosimeter cavity is located such that when the radiation dosimeter is inserted into the dosimeter cavity, the radiation dosimeter is located proximal to the surface of the patient.

3. The apparatus according to claim 1 wherein a shape of the dosimeter cavity is configured such that only a selected type of radiation dosimeter will fit within the dosimeter cavity.

4. The apparatus according to claim 1 further comprising a restraining mechanism for removably restraining the radiation dosimeter within said dosimeter cavity.

5. The apparatus according to claim 1 wherein said dosimeter cavity is configured for removable insertion of a radiation dosimeter type selected from the group consisting of ionization chambers, diodes, metal-oxide-semiconductor field-effect transistors, radiographic film, radiochromic film, diamond detectors, and optically stimulated luminescence dosimeters.

6. The apparatus according to claim 1 wherein said outer beam-incident surface is shaped to modulate a dose delivered to the patient when said inner patient-facing surface is placed against the patient and electron radiation is transmitted through said patient-specific radiation bolus during an electron radiation therapy procedure.

7. The apparatus according to claim 1 wherein said patient-specific radiation bolus comprises multiple layers formed via a three-dimensional printing process.

8. The apparatus according to claim 1 further comprising a patient-specific immobilization mesh configured to support the patient-specific radiation bolus against the surface of the patient, wherein said patient-specific radiation bolus is integrally formed with said patient-specific immobilization mesh, and wherein said patient-specific immobilization mesh conforms to the surface of the patient.

9. The apparatus according to claim 8 further comprising a securing means to secure said patient-specific immobilization mesh relative to the patient.

10. A method of performing in-vivo dosimetry during a radiation therapy procedure, the method comprising:
providing an apparatus according to claim 1;
inserting a radiation dosimeter into the dosimeter cavity;
gathering in-vivo dosimetry data from the radiation dosimeter during the radiation therapy procedure; and
after performing the radiation therapy procedure, removing the radiation dosimeter from the dosimeter cavity.

11. A method of fabricating a patient-specific radiation bolus, the method comprising:
processing data comprising (i) three-dimensional scan data associated with a patient, (ii) a planning target volume, and (iii) a first dose calculation associated with a treatment goal to obtain a target bolus model, the target bolus model having an inner patient-facing surface and an outer beam-incident surface, wherein the inner patient-facing surface is configured to conform to a surface of the patient and the outer beam-incident surface is configured spatially modulate the dose delivered to the patient during a radiation therapy procedure;

modifying the target bolus model to obtain a modified target bolus model configured such that a patient-specific radiation bolus fabricated according to the modified target bolus model includes a dosimeter cavity configured for removable insertion of a radiation dosimeter for performing in-vivo dosimetry during the radiation therapy procedure, and such that the radiation dosimeter is removable from said dosimeter cavity after the radiation therapy procedure; and fabricating the patient-specific radiation bolus according to the modified target bolus model;

wherein the dosimeter cavity is located such that when the radiation dosimeter is inserted into the patient-specific radiation bolus and the patient-specific radiation bolus is contacted with the patient, the radiation dosimeter resides proximal to the surface of the patient.

12. The method according to claim 11 wherein the patient-specific radiation bolus is fabricated by three-dimensional printing.

13. The method according to claim 11 wherein the target bolus model is modified such that when the radiation dosimeter is inserted into the dosimeter cavity of the patient-specific radiation bolus, the radiation dosimeter is located proximal to the surface of the patient.

14. The method according to claim 11 wherein the target bolus model is modified such that only a selected type of radiation dosimeter will fit within the dosimeter cavity of the patient-specific radiation bolus.

15. The method according to claim 11 wherein the patient-specific radiation bolus is fabricated to include a restraining mechanism for removably restraining the radiation dosimeter within the dosimeter cavity.

16. The method according to claim 11 wherein the target bolus model is modified such that the dosimeter cavity of the patient-specific radiation bolus is configured for removable insertion of a radiation dosimeter type selected from the group consisting of ionization chambers, diodes, metal-oxide-semiconductor field-effect transistors, radiographic film, radiochromic film, diamond detectors, and optically stimulated luminescence dosimeters.

17. The method according to claim 11 wherein the target bolus model is generated according to an electron radiation therapy procedure.

18. The method according to claim 11 further comprising processing the three-dimensional scan data associated with the patient to obtain a model of a patient-specific immobilization mesh configured to support the patient-specific radiation bolus against the surface of the patient; and fabricating the patient-specific immobilization mesh such that the patient-specific radiation bolus is supported by and integrally formed with the patient-specific immobilization mesh.

19. The method according to claim 18 wherein the patient-specific immobilization mesh and the patient-specific radiation bolus are formed via three-dimensional printing.

20. The method according to claim 18 wherein the patient-specific immobilization mesh is fabricated to include a securing means to secure the patient-specific immobilization mesh relative to the patient.

* * * * *